US005163436A

United States Patent [19]

Saitoh et al.

[11] Patent Number: 5,163,436

[45] Date of Patent: Nov. 17, 1992

[54] ULTRASONIC PROBE SYSTEM

[75] Inventors: Shiroh Saitoh, Yokohama; Mamoru Izumi, Tokyo; Syuzi Suzuki, Yokohama; Shinichi Hashimoto, Kawasaki, all of Japan

[73] Assignee: Kabushiki Kaisha Toshiba, Kawasaki, Japan

[21] Appl. No.: 673,086

[22] Filed: Mar. 21, 1991

[30] Foreign Application Priority Data

Mar. 28, 1990 [JP] Japan .................................. 2-76617

[51] Int. Cl.[5] .............................................. A61B 8/00

[52] U.S. Cl. ......................... 128/662.03; 128/663.01; 73/642; 310/335

[58] Field of Search ...................... 128/661.01, 662.03, 128/663.01; 73/642; 310/335, 366

[56] References Cited

U.S. PATENT DOCUMENTS

| | | | |
|---|---|---|---|
| 4,101,795 | 7/1978 | Fukumoto et al. | 128/662.03 |
| 4,145,931 | 3/1979 | Tancrell | 128/661.01 |
| 4,211,948 | 7/1980 | Smith et al. | 128/662.03 |
| 4,277,711 | 7/1981 | Hanafy | 128/662.03 |
| 4,385,255 | 5/1983 | Yamaguchi et al. | 310/335 |
| 4,616,152 | 10/1986 | Saito et al. | 310/335 |
| 4,845,399 | 7/1989 | Yasuda et al. | 310/366 |

FOREIGN PATENT DOCUMENTS

| | | | |
|---|---|---|---|
| 0190948 | 2/1986 | European Pat. Off. | 128/662.03 |
| 2044582 | 10/1980 | United Kingdom | 128/662.03 |
| 2083695 | 3/1982 | United Kingdom | 128/662.03 |

OTHER PUBLICATIONS

Patent Abstracts of Japan, vol. 9, No. 248 (E'347) [1971], Oct. 4, 1985; & JP-A-60 98 799 (Olympus Kogaku Kogyo) Jan. 6, 1985.

Patent Abstracts of Japan, vol. 7, No. 154 (E-185 [1299], Jul. 6, 1983; & JP-A-58 63 300 (Keisuke Honda) Apr. 15, 1983.

*Primary Examiner*—William E. Kamm
*Assistant Examiner*—George Manuel
*Attorney, Agent, or Firm*—Oblon, Spivak, McClelland, Maier & Neustadt

[57] ABSTRACT

An ultrasonic probe system is disclosed, which is designed to allow connection of a DC power supply capable of applying a voltage higher than the coercive electric field of each of a plurality of piezoelectric layers thereto, and includes a polarization turn over circuit means for, when the DC power supply is driven, turning over the polarity of the DC power supply so as to direct electric fields of every two adjacent layers constituting the piezoelectric layers in substantially opposite directions or electric fields of all the layers in the same direction. When the polarization turn over circuit means turns over the polarity of a voltage to be applied to direct electric fields of every two adjacent layers of the piezoelectric layers in substantially opposite directions or electric fields of all the layers in the same direction, the polarization turn over circuit means performs control to apply the voltage during a blanking time of an operating time of the system, thereby performing conversion of a resonance frequency, and selectively generating ultrasonic waves having a plurality of different frequencies.

16 Claims, 5 Drawing Sheets

ULTRASONIC PROBE SYSTEM

BACKGROUND OF THE INVENTION

1. Field of the Invention

The present invention relates to an ultrasonic probe used for an ultrasonic test apparatus and, more particularly, to an ultrasonic probe system which is constituted by a stacked piezoelectric element and is capable of transmitting/receiving ultrasonic waves having different frequencies.

2. Description of the Related Art

A detailed description of the prior art is available from the following references:

(1) Japanese Patent Disclosure (Koukai) No. 60-41399

(2) Japanese Patent Disclosure (Koukai) No. 61-69298

An ultrasonic probe has a probe head mainly constituted by a piezoelectric element. This ultrasonic probe is used to obtain image data representing the internal state of a target object by radiating ultrasonic waves onto the target object and immediately receiving waves reflected from interfaces of the target object which have different acoustic impedances. An ultrasonic test apparatus using such an ultrasonic probe is used in practice as, e.g., a medical diagnosing apparatus for examining the inside of a human body, or an industrial test apparatus for inspecting flaws in welded metal portions.

The diagnosing function of a medical diagnosing apparatus has been greatly improved owing to the development of "the color flow mapping (CFM) method" in addition to photography of a tomographic image (B mode image) of a human body. In this CFM method, blood flow rates in a heart, a liver, a carotid artery, and the like as targets are two-dimensionally displayed in color by using the Doppler effect. Recently, the CFM method has been used to diagnose all kinds of internal organs of a human body, such as the uterus, the kidney, and the pancreas. Further studies of the CFM method are now in progress to allow observation of even the movement of a coronary blood flow.

With regard to the above-mentioned B mode image, i.e., a tomographic image of a human body, it is required that a high-resolution image be obtained with high sensitivity to allow an operator to clearly observe a physical change or a cavity as a slight morbid alteration. In the Doppler mode for acquiring a CFM image or the like, since echoes (waves) reflected by, e.g., microscopic blood cells, each having a diameter of several μm, are used, the resulting signal level is lower than that obtained in the B mode described above. For this reason, high-sensitivity performance is especially required. In many cases, a reference frequency in this Doppler mode is set to be lower than the center frequency in the frequency band of an ultrasonic probe. This is because a frequency component exhibiting small attenuation is used to suppress the influences, of ultrasonic attenuation through a living body, which cause a decrease in S/N ratio. Therefore, providing that ultrasonic waves having two different types of frequency components can be transmitted/received by a single ultrasonic probe, both a high-resolution B mode image constituted by high-frequency components and a high-sensitivity Doppler image constituted by low-frequency components can be obtained. As probes having such functions, "duplex type ultrasonic probes" are available from various manufacturers. A duplex type ultrasonic probe is designed such that two types of vibrators having different resonance frequencies are arranged in one ultrasonic probe. Since an ultrasonic probe of this type uses different types of vibrators, ultrasonic transmission/reception planes are set at different positions. For this reason, tomographic images of the same portion cannot be observed. Under the circumstances, a method of transmitting/receiving ultrasonic waves in two types of frequency bands by using a single vibrator has been proposed, which uses a stacked piezoelectric element disclosed in Japanese Patent Disclosure (Koukai) No. 60-41399. Two types of frequency bands can be separated from each other by using a combination of an ultrasonic probe of this type, a driving pulser, and a filter. As a result, a B mode signal and a Doppler signal can be respectively acquired from high-frequency components and low-frequency components. However, in the ultrasonic probe having the above-described arrangement, since the electromechanical coupling efficiency of one piezoelectric element is divided into substantially halves, the high-frequency side frequency band is narrowed, and the remaining time (duration) of an echo signal is prolonged. For this reason, even if a B mode image is obtained by using high-frequency components to ensure high resolution, the resulting resolution is not so high as expected. That is, there is a room for improvement in this point. In addition, since low-frequency components are generally decreased in number as the frequency band becomes narrower, the S/N ratio is decreased, resulting in insufficient penetration. This is because an echo signal reflected by a portion located deep in a living body is mainly constituted by frequency components lower than the center frequency of transmitted ultrasonic waves. The specific band width of frequency components, which is required to obtain a good B mode image, is 40% or more of its center frequency. Assume that a single-layered piezoelectric element is used. In this case, a specific band width with respect to a center frequency at −6 dB is 40 to 50% in one-layer matching, and 60 to 70% in two-layer matching. In contrast to this, if the stacked piezoelectric element having the above-described arrangement is used, specific band widths of 25% and 35% are respectively set in one-layer matching and two-layer matching. That is, if only the stacked piezoelectric element is used, the obtained specific band width is only about ½ that obtained when the single-layered piezoelectric element is used.

An increase in sensitivity may be realized by increasing a driving voltage. This method, however, is also limited by the problem of heat generated by a piezoelectric element. Another problem posed in the method of obtaining two types of frequency bands by using a single ultrasonic probe is that the same portion cannot be observed because of the use of a plurality of vibrators having different resonance frequencies. As described above, in order to solve this problem, the stacked piezoelectric element is disclosed in Japanese Patent Disclosure (Koukai) No. 60-41399, which is obtained by stacking piezoelectric elements, each having substantially the same thickness as that of the single-layered piezoelectric element and consisting of substantially the same material as therefor. This element, however, poses the problem of a narrow specific band of high-frequency components.

As described above, when ultrasonic waves in two types of frequency bands are to be acquired by one ultrasonic probe, the same portion of a target object cannot be observed with a probe head constituted by a plurality of vibrators having different resonance frequencies. In the stacked piezoelectric element disclosed in Japanese Patent Disclosure (Koukai) No. 60-41399 to solve this problem, which is obtained by stacking layers, each having substantially the same thickness as that of the single-layered piezoelectric element and consisting of substantially the same material as therefor, the specific band of high-frequency components is too narrow.

SUMMARY OF THE INVENTION

It is an object of the present invention to provide an ultrasonic probe system including an ultrasonic probe which easily allows an increase in transmission frequency without posing problems in terms of manufacture and characteristics.

It is another object of the present invention to provide an ultrasonic probe system which allows an increase in sensitivity of reception performance in addition to an increase in transmission frequency, can transmit/receive two types of ultrasonic waves through the same plane of a probe, and has frequency characteristics exhibiting a sufficiently large band width of high-frequency components.

In order to solve the above-described problems and achieve the above objects, the following means are employed in the ultrasonic probe system according to the present invention. A probe head is constituted by a stacked piezoelectric element formed by stacking a plurality of piezoelectric layers such that the polarization directions of every two adjacent piezoelectric layers are opposite to each other or the polarization directions of all the piezoelectric layers coincide with each other, and bonding electrodes to two end faces of the stacked layers in the stacking direction and to the interface between the respective piezoelectric layers. The probe head is designed to allow connection of a DC power supply capable of applying a voltage higher than the coercive electric field of each piezoelectric member to one set of every other stacked piezoelectric layers and capable of changing the polarity of the voltage.

In addition, this probe head is constituted by a piezoelectric layer formed by stacking a plurality of piezoelectric members having predetermined polarization directions and the same thickness. The ultrasonic probe system is designed such that when a voltage higher than the coercive electric field of the piezoelectric layer is applied to each layer thereof, the polarity of the voltage is controlled to direct the electric fields of every two adjacent layers constituting the piezoelectric layer in substantially opposite directions or the electric fields of all the layers to the same direction, thereby selectively generating ultrasonic waves having a plurality of different frequencies.

That is, in this arrangement, a turn over circuit and a DC power supply are connected to the stacked piezoelectric element, which is formed by stacking the plurality of piezoelectric layers on each other and bonding the electrodes to the two end faces of the stacked piezoelectric layers in the stacking direction and to the interface between the respective piezoelectric layers, so that the voltage higher than the coercive electric field of the piezoelectric member is applied to one set of every other stacked piezoelectric layers such that the polarization directions of every two adjacent piezoelectric layers are opposite to each other or the polarization directions of all the piezoelectric layers coincide with each other, and the polarity of the voltage is changed to change the direction of a corresponding electric field.

In the ultrasonic probe of the present invention, since a DC power supply capable of manually or automatically turning its polarity over is connected to the stacked piezoelectric element, when the voltage higher than the coercive electric field is applied to one set of every other stacked piezoelectric layers, the minimum (fundamental) resonance frequency differs depending on whether the polarization directions of one set of every other piezoelectric layers to which the DC power supply is connected coincide or are opposite to those of the other set of every other piezoelectric layers to which the DC power supply is not connected. If the thickness of each piezoelectric layer is represented by t, the number of layers is represented by n, and the sound velocity of the piezoelectric member is represented by v, a fundamental resonance frequency f0, when all the polarization directions coincide with each other, satisfies the following equation:

$$v/2nt = f0$$

In contrast to this, if the polarization directions of every two adjacent piezoelectric layers are opposite to each other, the following equation is established:

$$nf0\ (=v/2t)$$

Such equations are established for the following reasons. If the polarization directions coincide with each other, the stacked piezoelectric element is equivalent to a one-layer piezoelectric element having a thickness nt. This means ½-wavelength resonance occurs in such a manner that the two end faces serve as loops of vibrations, and the middle point in the direction of thickness serves as a node. In contrast to this, assume that the polarization directions of every two adjacent piezoelectric layers are opposite to each other. In this case, when an arbitrary piezoelectric layer extends, an adjacent piezoelectric layer contracts. Therefore, n/2-wavelength resonance occurs in such a manner that the two end faces of the piezoelectric element in the direction of thickness serve as loops of vibrations, and the middle point serves as a node. Therefore, the resulting resonance frequency is n times that obtained when the polarization directions coincide with each other.

The present invention is characterized in that this resonance frequency conversion is performed by supplying a polarization turn over pulse and a sending pulse generated by a pulser constituting this ultrasonic probe system, and a "turn over" operation is performed within a blanking time, of a so-called system operating time, immediately before the reception mode of the system. This "blanking time" is a setting time of the system, during which data transmission and the like are performed. Although the blanking time varies depending on the type of an ultrasonic probe or a diagnosing apparatus, it is normally set to be 20 to 40 μs (see FIG. 5). Since a sending pulse is supplied to the ultrasonic probe within 10 μs after the end of this blanking time, the duration of time in which no transmission/reception of ultrasonic waves is performed (actual blanking time) is 10 to 30 μs. Since the polarization of each piezoelectric layer can be turned over by applying the voltage higher than the coercive electric field for several μs, this operation can be performed within 10 to 30 μs, for which no transmission/reception is performed. As a result, since the frequencies of sending ultrasonic waves can be switched at the same timing as that in a conventional diagnosing apparatus, a high-resolution, high-frequency B mode signal and a high-sensitivity, low-frequency Doppler signal can be acquired at the same timing as that in the conventional diagnosing apparatus. Therefore, a B mode image constituted by this high-frequency wave and a CFM image constituted by this low-frequency wave can be obtained in real time.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

Figure 1:
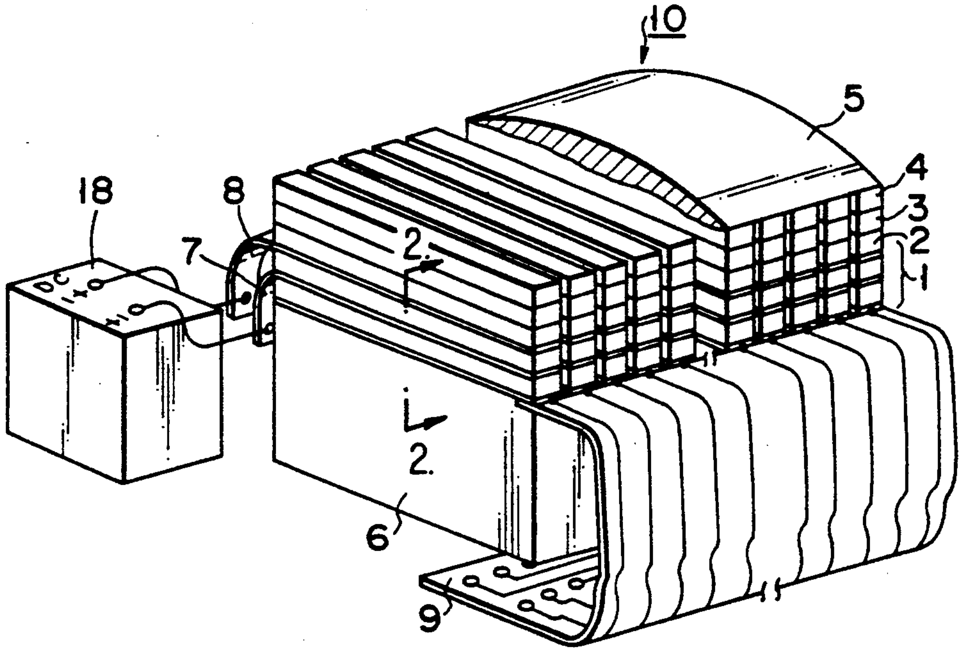
FIG. 1 is a perspective view showing a schematic arrangement of an ultrasonic probe according to the first embodiment of the present invention.

In an ultrasonic probe system according to the first embodiment of the present invention shown in FIG. 1, acoustic matching layers 2, 3, and 4 and an acoustic lens 5 are formed on the ultrasonic radiation side of a stacked piezoelectric element 1, while a backing member 6 as a base of a probe head is formed on the rear surface side. The stacked piezoelectric element 1 is formed by stacking two piezoelectric layers on each other. An inner electrode is bonded to the interface between these piezoelectric layers, whereas outer electrodes are respectively bonded to both end faces of the element 1 in the stacking direction, i.e., one each of the upper and lower outer electrodes are formed. The acoustic matching layers 2, 3, and 4 and the acoustic lens 5 are formed on the piezoelectric layer, and the backing member 6 is formed under the piezoelectric layer. With this arrangement, the piezoelectric layer is sandwiched between these upper and lower members, thus constituting a probe head having an illustrated integrated structure.

The thicknesses of the three matching layers 2, 3, and 4 are set to ensure matching on the high-frequency side. Such setting is performed to acquire a B mode signal on the high-frequency side and to broaden a sensitivity band.

In this ultrasonic probe, the stacked layers except for the acoustic lens 5 on the uppermost portion and the backing member 6 are formed into strips. A common ground electrode line (not shown) is soldered to one outer electrode, and signal lines of a flexible print plate 9 are soldered to the other outer electrode. More specifically, the pitch of the signal lines of the flexible print plate 9 is set to be 0.15 mm, which is an optimal value calculated in relation to a cutting operation by a dicing machine using a 30-$\mu$ thick blade used for forming the above-mentioned strips.

A DC power supply 18 capable of turning over the polarity is connected to the stacked piezoelectric element through polarity turn over common electrode lines 7 and 8 between one outer electrode and the inner electrode of the stacked piezoelectric layer to supply power to the electrodes of the head. When the polarity of the DC power supply 18 connected to the stacked piezoelectric element is manually or automatically turned over, the polarization directions of every two adjacent stacked layers ca be changed to substantially opposite directions regardless of whether the initial polarization directions of the adjacent piezoelectric layers are the same or opposite to each other. Therefore no special consideration need be given to the initial polarization directions of the piezoelectric layers connected to the DC power supply 18 capable of turning polarity over.

Figure 2A:
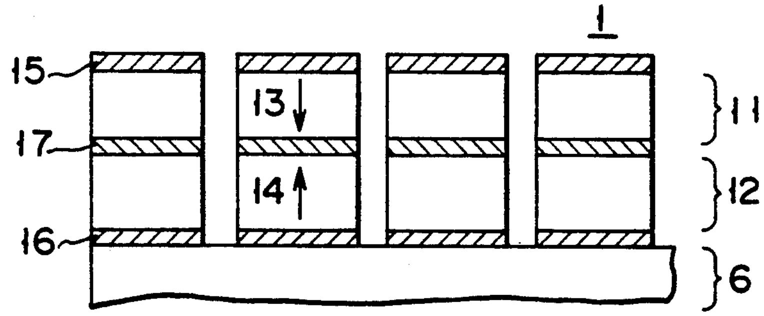
FIGS. 2A and 2B are enlarged sectional views, of a stacked piezoelectric element in FIG. 1, taken along a line 2—2'.
Figure 2B:
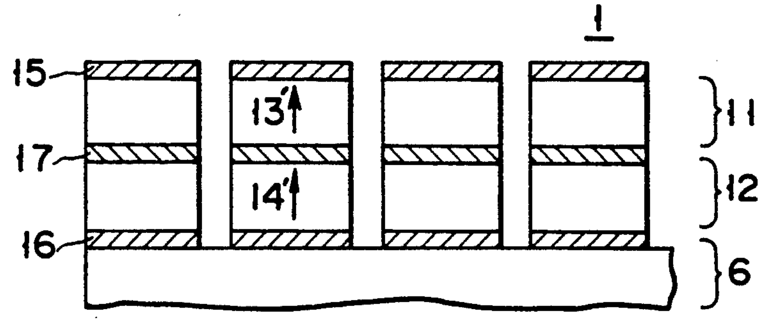

FIGS. 2A and 2B are enlarged sectional views, of the stacked piezoelectric element in FIG. 1, taken along a line 2—2'. As shown in FIG. 2A, in this stacked piezoelectric element' for example, two piezoelectric layers 11 and 12 are stacked on each other such that polarization directions (arrows) 13 and 14 oppose each other in an initial state. Outer electrodes 15 and 16 are bonded to two end faces of the element, i.e., the upper surface of the piezoelectric layer 11 and the lower surface of the piezoelectric layer 12, and an inner electrode 17 is bonded to the interface between the piezoelectric layers 11 and 12. In the embodiment shown in FIG. 2A, the adjacent two piezoelectric layers have opposite polarization directions. However, the initial polarization directions of the piezoelectric layers of a stacked piezoelectric element may have same polarization direction, as polarization directions 13' and 14' in FIG. 2B, as long as the piezoelectric layers are connected to the abovementioned DC power supply capable of turning polarity over.

Each of the piezoelectric layers 11 and 12 is composed of a piezoelectric ceramic material, called a PZT ceramic material having a specific permittivity of 2,000, to have a thickness of 200 $\mu$m. The cross sections of the stacked piezoelectric element 1 constituting this probe head are arranged in an array of strips, as shown in FIGS. 2A and 2B. In the manufacture of the probe head, therefore, the stacked piezoelectric element including matching layers (not shown), which are bonded to the upper surface, is cut in the stacking direction (i.e., vertical direction) by a dicing machine using a blade. Thereafter, the cut portions are horizontally arranged at a predetermined pitch. In this case, the pitch is set to be 0.15 mm.

Figure 3A:
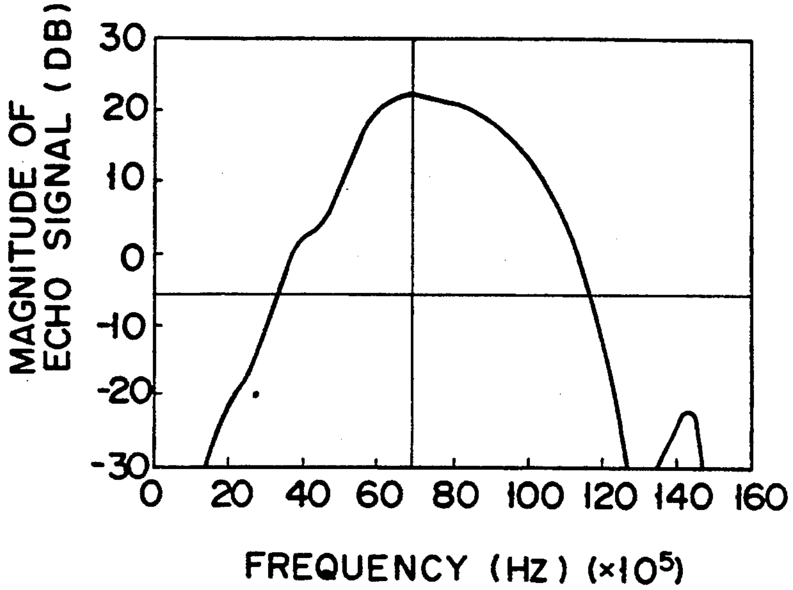
FIG. 3A is graph showing the frequency spectrum of an echo wave measured by the "pulse echo method" when every two adjacent piezoelectric layers have opposite polarization directions.

FIG. 3A is a graph showing the frequency spectrum of an echo wave reflected by a reflector in water and measured by the "pulse echo method". According to this graph, a center frequency is about 7 MHz (an actual measurement value: 7.54 MHz), and a specific band of −6 dB corresponds to 52.9% of the center frequency. It is apparent from the values indicated by the graph that a frequency band wide enough to obtain a good B mode image by using an ultrasonic imaging apparatus using an ultrasonic probe can be obtained.

Figure 3B:
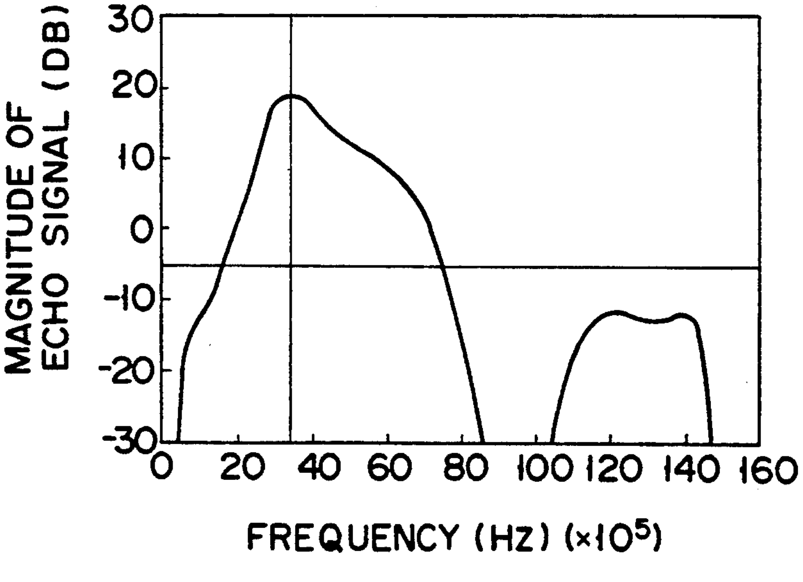
FIG. 3B is a graph showing a frequency spectrum measured by the "pulse echo method" when every two adjacent piezoelectric layers have the same polarization direction.

FIG. 3B is a graph showing the frequency spectrum of an echo wave measured by the "pulse echo method", more specifically, a characteristic curve obtained when the polarization direction of a given piezoelectric layer is turned over by applying a DC voltage of 400 V to the layer for about 10 seconds by using a DC power supply capable of turning over polarity so that the polarization directions of all the piezoelectric layers are set to be the same. As indicated by this graph, a center frequency of about 3.5 MHz (an actual measurement value: 3.71 MHz) is set, and a specific band of −6 dB corresponds to 51.9% of the center frequency.

When all the polarization directions are changed to the same direction by using this DC power supply, the center frequency of an echo wave is reduced to about ½. If a voltage having the opposite polarity is applied to a corresponding piezoelectric layer in this state, the polarization directions are restored to the initial state in this embodiment, i.e., the opposite directions.

As is apparent from the above experimental results, two different types of ultrasonic waves can be acquired by the same plane of one ultrasonic probe.

The present invention is not limited to the embodiment described above. Various changes and modifications can be made within the spirit and scope of the invention. For example, in this embodiment, the two-layered stacked piezoelectric element is used. However, a stacked piezoelectric constituted by three or more layers may be used.

According to the first embodiment of the present invention, a plurality of piezoelectric layers are stacked on each other such that the polarization directions of every two adjacent layers are opposite to each other or the polarization directions of all the layers are the same, and a DC power supply capable of turning over the polarity by applying a voltage higher than the coercive electric field of a piezoelectric member to one set of every other layers of a stacked piezoelectric element in which electrodes are bonded to the two end faces in the stacking direction and the interface between the piezoelectric layers can be connected to the element. With this arrangement, the polarization directions of the respective piezoelectric layers of the stacked piezoelectric element can be set to substantially desired directions, thereby realizing an ultrasonic probe system which can be used without limitation in terms of the initial polarization directions of piezoelectric layers. In addition, an ultrasonic probe system can be provided, which can transmit/receive ultrasonic waves having two different types of frequencies through the same plane of a probe head of an ultrasonic probe, and can simultaneously acquire a wide-band B mode signal in a high-frequency region and a high-sensitivity Doppler signal in a low-frequency region.

Figure 4:
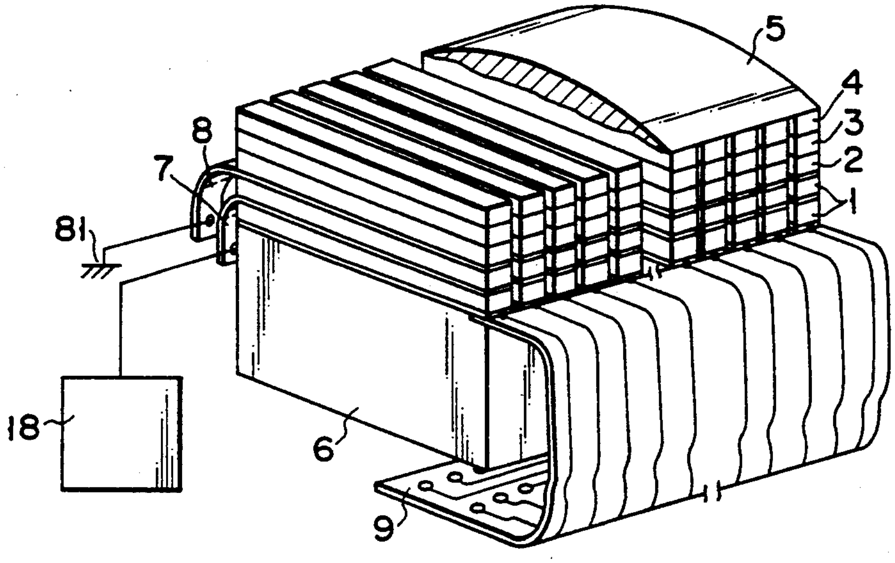
FIG. 4 is a perspective view showing a schematic arrangement of an ultrasonic probe according to the second embodiment of the present invention.

FIG. 4 is a perspective view showing a schematic arrangement of an ultrasonic probe according to the second embodiment of the present invention. Acoustic matching layers 2, 3, and 4 and an acoustic lens 5 are formed on the ultrasonic radiation side of a stacked piezoelectric element 1, whereas a backing member 6 as a base of a probe head is formed on the rear surface side. The stacked piezoelectric element 1 is formed by stacking two piezoelectric layers on each other. An inner electrode is bonded to the interface between these piezoelectric layers, whereas outer electrodes are respectively bonded to both end faces of the element 1 in the stacking direction, i.e., one each of the upper and lower outer electrodes are formed. The acoustic matching layers 2, 3, and 4 and the acoustic lens 5 as upper members and the backing member 6 as a lower member are formed to sandwich the stacked piezoelectric layer, thus constituting a probe head having an integrated structure, as shown in FIG. 4.

The thicknesses of the three matching layers 2, 3, and 4 are set to ensure matching on the high-frequency side. Such setting is performed to acquire a B mode signal on the high-frequency side and to broaden a sensitivity band.

In this ultrasonic probe, the stacked layers except for the acoustic lens 5 on the uppermost portion and the backing member 6 are formed into strips. A common ground electrode line is soldered to one outer electrode, and signal lines of a flexible print plate 9 are soldered to the other outer electrode. More specifically, the pitch of the signal lines of the flexible print plate 9 is set to be 0.15 mm, which is an optimal value calculated in relation to a cutting operation by a dicing machine using a 30-μ thick blade used for forming the above-mentioned strips.

A polarization turn over circuit 18 capable of turning over the polarity is used to supply power to the electrodes of this head. The circuit 18 includes a DC power supply connected to the stacked piezoelectric element through polarity turn over common electrode lines 7 and 8 between one outer electrode and the inner electrode of the stacked piezoelectric layer. When the polarity of the DC power supply of the polarization turn over circuit 18 connected to the stacked piezoelectric element is manually or automatically turned over, the polarization directions of every two adjacent stacked layers can be changed to opposite directions regardless of whether the initial polarization directions of the adjacent piezoelectric layers are the same or opposite to each other. Therefore, no special consideration need be given to the initial polarization directions of the piezoelectric layers connected to the DC power supply.

Figure 5:
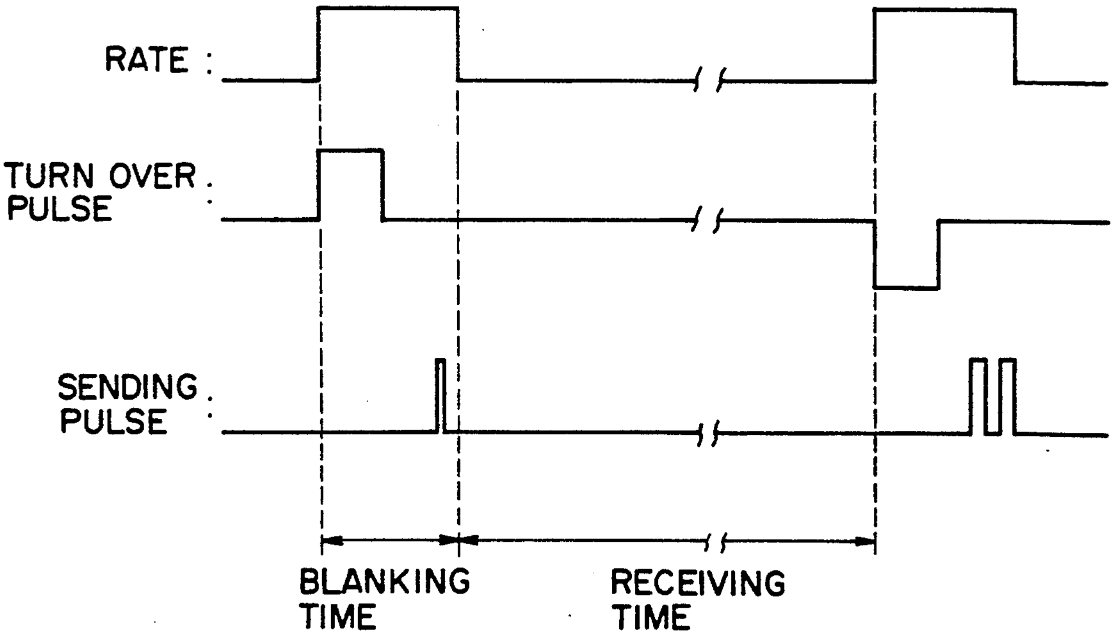
FIG. 5 is a timing chart of various types of pulses for driving the ultrasonic probe.

FIG. 5 is a timing chart of voltage pulses for driving the ultrasonic probe according to the present invention. A blanking time as a setting time of the system is 30 μs. A sending pulse is applied 10 μs after the end of this blanking time. Therefore, a polarization turn over operation has a margin of about 20 μs. In this embodiment, a turn over pulse is applied only for 15 μs. Since this piezoelectric element has a coercive electric field of 1 kV/mm, a voltage of ∓200 V is applied. Note that the polarization turn over circuit is constituted by an FET switch.

Figure 6A:
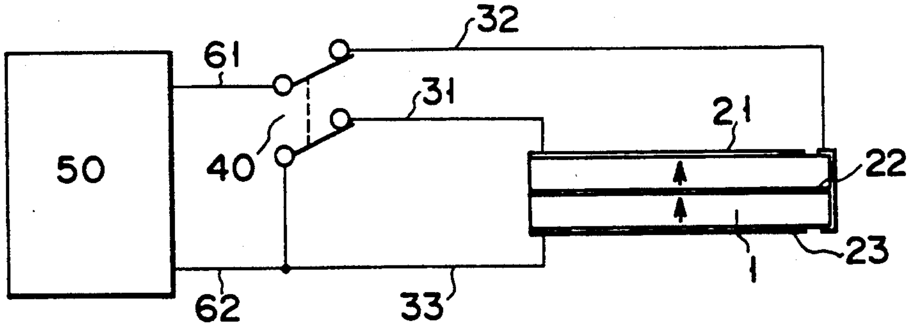
FIGS. 6A and 6B are circuit diagrams, each showing a schematic connecting state of a polarization turn over circuit of the ultrasonic probe according to the present invention.
Figure 6B:
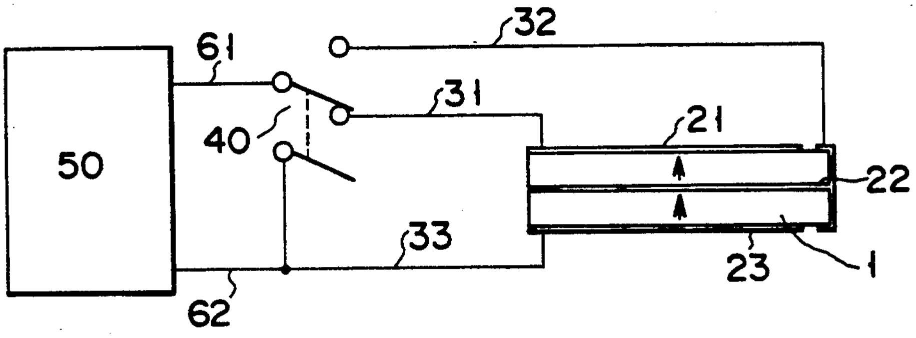

FIGS. 6A and 6B are circuit diagrams, each showing a schematic connecting state of an ultrasonic probe according to the present invention. A piezoelectric vibrator 1 is constituted by a stacked layer (piezoelectric layer) formed by bonding two piezoelectric ceramic members, as piezoelectric elements having substantially the same thickness, to each other in the direction of thickness. Two different types of frequency bands are excited from the single vibrator 1 by controlling the polarities of driving pulses to be respectively applied to electrodes 21, 22, and 23 formed on the interfaces between the layers of this two-layer piezoelectric vibrator 1. In the connecting states shown in FIGS. 6A and 6B, the polarization directions of the respective piezoelectric ceramic layers are initially set to be the same direction, and leads 31, 32, and 33 are respectively extracted from the electrodes 21, 22, and 23 to form a three-terminal connecting circuit. A pulser/receiver circuit for processing reception signals of a driving pulse source and the vibrator has two terminals, i.e., a GND terminal 62 and a signal terminal 61. The three terminals of the vibrator 1 are connected to the two terminals of the pulser/receiver circuit through two switches, as shown in FIGS. 6A and 6B. Since the resonance frequency of the vibrator 1 is changed by operating these switches, two types of frequencies can be excited. The principle of this operation will be described below with reference to FIGS. 7A to 7E.

Figure 7A:
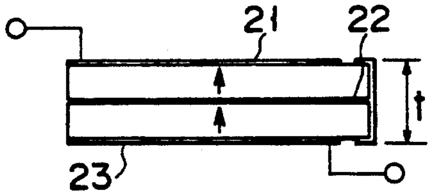
FIG. 7A is a wiring diagram showing a piezoelectric layer having a two-layered structure.
Figure 7B:
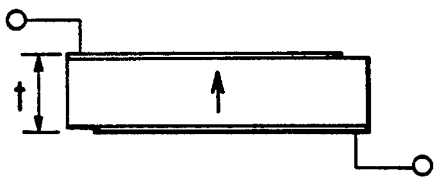
FIG. 7B is a wiring diagram showing a piezoelectric layer having a one-layered structure.

FIG. 7A shows a piezoelectric vibrator of this embodiment. FIG. 7B shows a single-layer piezoelectric vibrator equivalent to the vibrator in FIG. 7A. Referring to FIG. 7A, a two-layered vibrator is designed such that the stacked layers have the same polarization direction, and a pulse is applied between electrodes 21 and 23 respectively formed on the upper and lower surfaces of the piezoelectric element. An inner electrode 22 is formed in an electrically floating state. In this case, since the resonance frequency of the vibrator is determined by a total thickness t of the two-layered vibrator, and the thickness of each electrode can be substantially neglected as compared with the thickness of the ceramic layer, the thickness of the vibrator in FIG. 7B is equivalent to the thickness t. Assume, in this case, that the resonance frequency and the electric impedance are respectively represented by f0 and Z0.

Figure 7C:
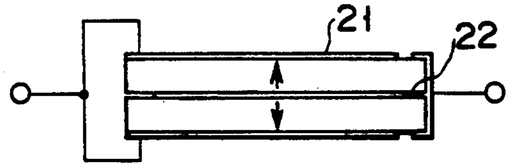
FIGS. 7C to 7E are wiring diagrams, each showing the polarization direction of each layer of the two-layered piezoelectric element.

FIG. 7C shows a modification in which a piezoelectric vibrator and electrodes are connected in a different manner. More specifically, FIG. 7C shows a piezoelectric element in which the two layers of a two-layered vibrator are stacked on each other to have opposite polarization directions. Electrodes 21 and 23 on the upper and lower surfaces of the element are commonly connected, and a pulse is applied between an inner electrode 22 and the electrodes 21 and 23. Similarly, in this case, electric field of a pulse is directed to the same direction as the polarization direction of each ceramic layer. Therefore, if the total thickness of the element is t, the resonance frequency is f0. However, the electric impedance between the two terminals is reduced to ¼ that of the element shown in FIGS. 7A and 7B. This is a low impedance effect due to the stacked structure.

Figure 7D:
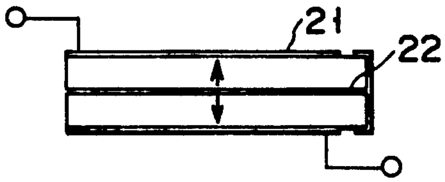

In the connecting structure shown in FIG. 7D as a modification, although stacked layers have opposite polarization directions, a pulse is applied between two surface electrodes 21 and 23. This arrangement is equivalent to a combination of a layer in which the directions of polarization and an electric field coincide with each other and a layer in which the directions of polarization and an electric field are opposite to each other (as disclosed in U.S. patent application Ser. No. 13,891,075). The resonance frequency of the element shown in FIG. 7D is given by 2f0 which is twice that of the element shown in FIG. 7A, providing that they have the same thickness. The electric impedance of this element is given by Z0 which is the same as that of the element in FIG. 7A.

Figure 7E:
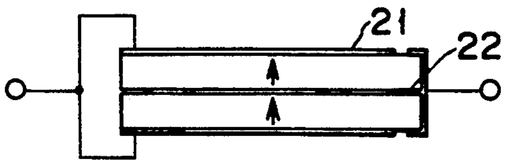

FIG. 7E shows a structure constituted by combination of a layer in which the directions of polarization and an electric field coincide with each other and a layer in which the directions of polarization and an electric field are opposite to each other. In this case, therefore, the resonance frequency is given by 2f0, similar to the element in FIG. 7D. In addition, the electric impedance is reduced to Z0/4, similar to the element shown in FIG. 7C. That is, the resonance frequency can be increased to a multiple of the number of layers, or the electric impedance can be reduce to 1/the square of the number of layers by a combination of the polarization direction of each layer of a multi-layered structure and an electric field direction.

With the arrangement described above, the resonance states of the stacked layers shown in FIGS. 7A to 7E can be selectively realized by a switching operation of a switch 40 shown in FIGS. 6A and 6B. With the arrangement shown in FIG. 7A, an ultrasonic probe having the resonance frequency f0 and the electric impedance Z0 can be realized. With the arrangement shown in FIG. 7B, an ultrasonic probe having the resonance frequency 2f0 and the electric impedance Z0/4 can be realized.

Figure 8:
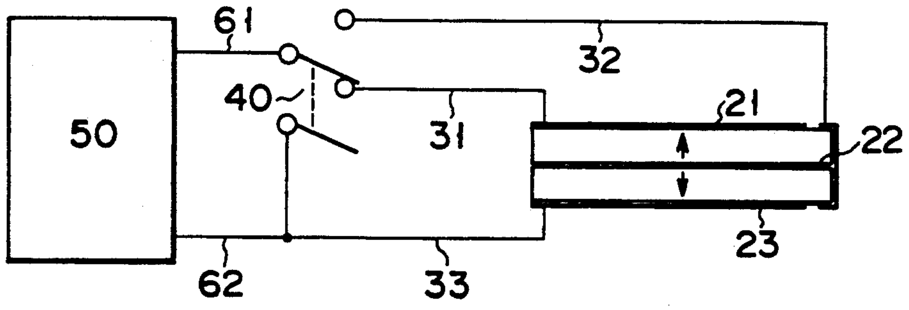
FIG. 8 is a schematic wiring diagram showing an ultrasonic probe system according to another embodiment of the ultrasonic probe shown in FIGS. 6A and 6B.

FIG. 8 shows still another embodiment of the present invention. If a stacked piezoelectric element is designed to be selectively switched to the resonance states of the stacked layers shown in FIGS. 7C and 7D, an ultrasonic probe system can be provided, in which two types of combinations of resonance frequencies and electric impedances, i.e., f0 and Z0/4, and 2f0 and Z0, can be selectively switched. As described above, if a two-layered vibrator consisting of two identical layers is formed into a three-terminal structure, and the application conditions of driving pulses are selectively switched, the resulting structure can be driven in two types of frequency bands including frequencies having a frequency ratio of 2. Although this switch is preferably arranged on the probe side, it may be arranged on the side of the diagnosing apparatus main body.

Figure 9:
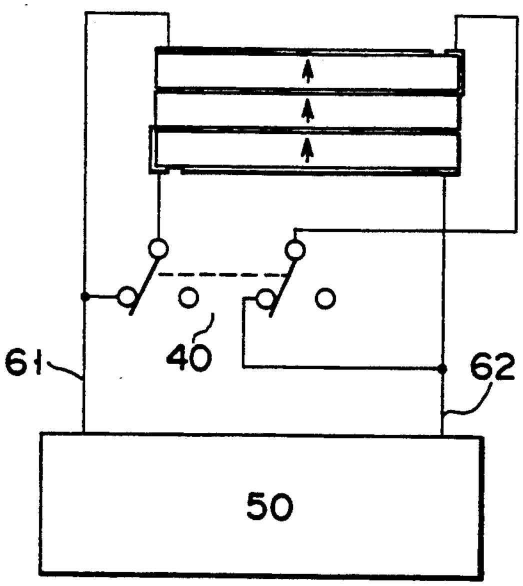
FIG. 9 is a schematic wiring diagram showing an ultrasonic probe system including a stacked piezoelectric element constituted by three layers according to still another embodiment of the present invention.

FIG. 9 shows an ultrasonic probe using a vibrator having a three-layered structure, which can be driven in two types of frequency bands including frequencies having a frequency ratio of 3 (3f0) by operating a switch.

As is apparent from the above description, by switching combinations of layers constituting a piezoelectric element and their polarities in accordance with a predetermined combination, ultrasonic waves having a plurality of different types of frequencies (two types in this embodiment) can be acquired through the same plane of the stacked electric member of one ultrasonic probe. In diagnosis, therefore, desired frequencies in these frequency bands can be arbitrarily selected and used in accordance with application purposes.

The present invention is not limited to the embodiment described above. Various changes and modifications can be made within the spirit and scope of the invention. For example, the stacked piezoelectric member has the two-layered structure in this embodiment. However, a stacked piezoelectric element consisting of three or more layers may be used.

According to the second embodiment of the present invention, a plurality of piezoelectric layers are stacked on each other such that the polarization directions of every two adjacent layers are opposite to each other or the polarization directions of all the layers coincide with each other. In addition, a DC power supply, which can apply a voltage higher than the coercive electric field of the piezoelectric member, to one set of every other piezoelectric layers of a stacked piezoelectric element, in which electrodes are bonded to the two end faces in the stacking direction and the interface between the piezoelectric layers, can be connected to the element through a polarization turn over circuit capable of turning over the polarity within a blanking time of the system. With this arrangement, the polarization direction of each piezoelectric layer of the stacked piezoelectric element can be set to a substantially desired direction, thereby realizing an ultrasonic probe system which can be used without being limited by the original polarization directions of the piezoelectric layers. In addition, an ultrasonic probe system can be provided, which has an ultrasonic probe capable of selectively transmitting/receiving ultrasonic waves having two different types of frequencies through the same plane of a probe head, and capable of simultaneously acquiring a wide-band B mode signal in a high-frequency region, and a high-sensitivity Doppler signal in a low-frequency region.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An ultrasonic probe system comprising:

probe head means for transmitting or receiving ultrasonic waves having different frequencies, said probe head means comprising, a stacked piezoelectric element including a plurality of piezoelectric layers for transmitting or receiving ultrasonic waves having different frequencies stacked on each other in a direction of thickness, a plurality of first electrodes bonded to opposed end faces of said plurality of piezoelectric layers in a stacking direction, and at least one second electrode bonded to an interface between said plurality of piezoelectric layers, ultrasonic focusing means bonded to an upper surface of said piezoelectric layers and having a convex surface directed outward, and wiring means connected to said first electrode of said piezoelectric layer; and control means for controlling said ultrasonic frequencies by controlling polarization directions of said plurality of piezoelectric layers.

2. The system according to claim 1, further comprising ultrasonic frequency matching means constituted by a plurality of layers bonded to one surface of said stacked piezoelectric element.

3. The system according to claim 1, further comprising head base means bonded to an opposing surface of said stacked piezoelectric element.

4. The system according to claim 3, wherein said stacked piezoelectric layers comprise a plurality of strips laid on said head base means, and a ground common electrode line is soldered to one of said first electrodes, and said wiring means comprises print wiring soldered to the other of said first electrodes.

5. The system according to claim 3, wherein said head base means is a backing member, said ultrasonic matching means is an acoustic matching layer, and said ultrasonic focusing means is an acoustic lens.

6. The system according to claim 1, wherein said stacked piezoelectric element comprises two piezoelectric layers, having almost the same thickness.

7. The system according to claim 1, wherein said control means comprises DC power supply means, connected to said first electrodes and said second electrodes, for applying a DC voltage to said first and second electrodes.

8. The system according to claim 1, wherein each of said plurality of piezoelectric layers consists of a piezoelectric ceramic material having a thickness of not more than 200 $\mu$m.

9. The system according to claim 1, wherein each of said piezoelectric layers consists of a PZT ceramic material having a specific permittivity of 2,000 and a thickness of 75 $\mu$m.

10. The system according to claim 1, wherein said stacked piezoelectric element comprises three piezoelectric layers stacked on each other, and said three piezoelectric layers have almost same thickness.

11. The system according to claim 1, comprising:

a DC power supply capable of applying a voltage higher than a coercive electric field of each of said piezoelectric layers connected to said first and second electrodes, and said control means comprising polarization turn over circuit means for, when said DC power supply is driven, turning over a polarity of said DC power supply so as to direct electric fields of every two adjacent layers constituting said piezoelectric layers in substantially opposite directions or electric fields of all the layers in the same direction, thereby selectively generating ultrasonic waves having a plurality of different frequencies.

12. The system according to claim 11, wherein when said polarization turn over circuit means turns over the polarity of a voltage to be applied to direct electric fields of every two adjacent layers of said piezoelectric layers in substantially opposite directions or electric fields of all the layers in a same direction, said polarization turn over circuit means performs control to apply the voltage during a blanking time of an operating time of said system, thereby performing conversion of a resonance frequency.

13. A system according to claim 11, further comprising ground means connected to one of said first electrodes or said at least one second electrode.

14. The system according to claim 11, wherein:

one of said first electrodes is an outer electrode connected to said wiring means, said second electrode is an inner electrode connected to said polarization turn over circuit means, said ultrasonic frequency matching means is an acoustic matching layer, said ultrasonic focusing means is an acoustic lens, said head base means is a backing member, said ground means is a ground plate connected to one of said first electrodes, and said wiring means comprises a flexible print board on which a print wiring pattern connected to said piezoelectric layers are formed.

15. An ultrasonic probe system for transmitting or receiving ultrasonic waves having different frequencies, comprising:

a stacked piezoelectric element comprising a plurality of piezoelectric layers stacked on each other such that polarization directions of every two adjacent layers are opposite to each other or polarization directions of all the layers coincide with each other, first electrodes respectively bonded to said piezoelectric layers and located at opposed ends in a stacking direction, and a second electrode being bonded to a portion between said two adjacent piezoelectric layers, and a DC power supply for supplying a voltage to each of said piezoelectric layers, the voltage being higher than a coercive electric field of each of said piezoelectric layers;

wherein said DC power supply is capable of applying a voltage higher than a coercive electric field of each of said plurality of piezoelectric layers to each of every other piezoelectric layer connected thereto, and said system further comprises polarization turn over means capable of turning over a plurality of the voltage applied by said DC power supply.

16. The ultrasonic probe system for transmitting or receiving ultrasonic waves having different frequencies, comprising:

a plurality of piezoelectric layers including a plurality of piezoelectric members having predetermined polarization directions and the same thickness stacked one upon the other;

a DC power supply for applying a voltage to each of said piezoelectric layers, the voltage being higher than a coercive electric field of each of said piezoelectric layers; and polarization turn over circuit means for changing the direction of electric field of all the layers by turning over the polarity of the voltage of said DC power supply so as to direct electric fields of every two adjacent layers constituting said piezoelectric layers in substantially opposite directions or electric fields of all the layers in the same direction thereby generating an ultrasonic wave having a frequency selected from a plurality of different frequencies.

* * * * *